United States Patent [19]
Sijmons

[11] Patent Number: 5,770,786
[45] Date of Patent: Jun. 23, 1998

[54] METHOD FOR THE ISOLATION AND/OR TESTING OF GENES AND PROMOTERS INVOLVED IN PLANT-NEMATODE INTERACTIONS USING PLANTS OF THE GENUS ARABIDOPSIS

[75] Inventor: Peter Christiaan Sijmons, Amsterdam, Netherlands

[73] Assignee: Mogen International N.V., Leiden, Netherlands

[21] Appl. No.: 122,456
[22] PCT Filed: Mar. 24, 1992
[86] PCT No.: PCT/EP92/00662
 § 371 Date: Jan. 5, 1994
 § 102(e) Date: Jan. 5, 1994
[87] PCT Pub. No.: WO92/17054
 PCT Pub. Date: Oct. 15, 1990

[30] Foreign Application Priority Data

Mar. 26, 1991 [EP] European Pat. Off. ............. 91200698

[51] Int. Cl.⁶ ............................. A01H 5/06; A01H 4/00; C12N 5/04; A01K 29/00
[52] U.S. Cl. ......................... 800/200; 435/410; 119/6.7
[58] Field of Search ................................... 800/205, 200, 800/DIG. 15; 435/240.4, 240.45, 240.54, 410, 419; 119/6.7

[56] References Cited

FOREIGN PATENT DOCUMENTS 8601074 2/1986 WIPO .
8810066 12/1988 WIPO .

OTHER PUBLICATIONS

D.A. Evans, et al. "Handbook of Plant Cell Culture" vol. 1, Technioques for Propagation and Breeding, MacMillian Publishing Co. N.Y., 1983, Chapter 32 pp. 880–903.

R.M. Riedel, et al. "Establishment of Nematode Germplasm Banks", Chapter 33, pp. 902–923.
"Breeding for Nematode Resistance", pp. 884–890, pp. 907–908, 909.
A. Barone, et al. 'Localization by Restriction . . . ' in: Molecular Gen Genetics, vol. 224, 1990, pp. 177–182.
C.O. Omwega, et al. 'A Single Dominant Gene . . . ' in: Phytopathology, vol. 80, No. 8, 1990, pp. 745–748.
R.B. Simpson and L.B. Johnson '*Arabidopsis thaliana* . . . ', in: Molecular Plant—Microbe Interactions, vol. 3, No. 4, 1990, pp. 233–237.
S.J. Turner, et al. 'Selection of Potato . . . ' in: Euphytica, vol. 32, 1983, pp. 911–917.
Goddjin, O.J.M. "Differentail Gene Expression . . . " The Plant Journal (1993) ₄ (S)863–873.
*Arabidopsis thaliana* as a New Model Host for Plant Parasitic Nematodes. Peter C. Sÿnious The Plant Journal (1991) 1(2) 245–254.
Potter et al; Nematode Pests of Vegetable Crops in Evans Trudgill and Webster (eds.) Plant Parasitic Nematodes in Temperate Agric. CAB Int'l, Willingford UK 1993.
Effects of Agar Brand & Concentration on the Tissue Culture Medium PC Debergh Physiol. Plant 59: 270–6 (1983).
In Vitro Culture of Plantation Crops Abraham D. Krikorian, Plant Cell & Tissue Culture, 497–537 (1994).
Ultrastructural Analysis of Giant Cell . . . C. Stender Flora (1982) 172: 223–233.
Wyss et al (1984) Physiol. Plant Pathol 25: 21–37.
Oue et al (1990) Plant Cell 2:837–848.

*Primary Examiner*—Elizabeth F. McElwain
*Attorney, Agent, or Firm*—Ladas & Parry

[57] ABSTRACT

The invention provides a method for infecting a root of a plant of the genus Arabidopsis with a plant parasitic nematode under monoxenic conditions, comprising the steps of: (a) contacting the root with a plant parasitic nematode in the presence of a gelling matrix dissolved in a nutrient medium that is substantially free of nematode inhibiting substances, and (b) allowing the nematode to infect the root by forming a feeding structure.

25 Claims, 7 Drawing Sheets

METHOD FOR THE ISOLATION AND/OR TESTING OF GENES AND PROMOTERS INVOLVED IN PLANT-NEMATODE INTERACTIONS USING PLANTS OF THE GENUS ARABIDOPSIS

TECHNICAL FIELD

This invention concerns a method for the culturing of nematodes on plants. The method finds specific use in the screening and isolation of nematode resistance genes and feeding-structure-specific genes and promoters.

BACKGROUND AND RELEVANT LITERATURE

Plant-parasitic nematodes worldwide cause diseases of nearly all crop plants of economic importance with estimated losses of about $5.8 billion/yr in the Unites States alone (Sasser and Freckman, 1987). While in tropical regions losses caused by nematodes are due mainly to root-knot nematodes (Meloidogyne), in Europe cyst nematodes of the genera Globodera and Heterodera are regarded as serious pests and important limiting factors in potato, rapeseed and sugarbeet cultivation, respectively. An increasing amount of crop damage is also being ascribed to free-living nematodes (e.g. Pratylenchus ssp). Only a small number of resistant crop varieties have emerged from breeding programmes for e.g. potato, sugarbeet, tomato, soybean and oil radish (Dropkin, 1988).

Through coevolution of plants and pathogens, plants have developed defense mechanisms against their pathogens. For successful infection of a plant, it is essential that the pathogen circumvents or suppresses the defense mechanism of the plant. In genetical terms, specific plant-pathogen interactions can be described by the gene-for-gene model. In this model an elicitor molecule (e), encoded by an avirulence gene (E) from the pathogen, interacts with a receptor molecule (r), encoded by a resistance gene (R) from the plant, which switches on the defense mechanism. Phenotypically, this mechanism becomes visible through the hypersensitive response (HR): local death of host cells around the site of infection which inhibits further development of the pathogen. The genetics of such gene-for-gene relationships are well documented for bacterial and fungal pathogens (Gabriel and Rolfe, 1990). Recent data from Whalen et al. (1991) indicate a degree of homology between resistance genes from Arabidopsis and soybean although these species are not related. The gene-for-gene model has been suggested for plant-nematode interactions (Jones et al. 1981; Turner et al., 1983). Furthermore, the hypersensitive response that is observed in cultivars that are resistant against a particular nematode species and for which the resistance has been mapped to a single dominant locus (Rick and Fobes, 1974; Delleart and Meijer, 1986; Omwega et al. 1990), indicates that gene-for-gene relationships may also function in plant-nematode interactions. The presence in soil of a resistance against nematodes in a particular variety persists under monoxenic culture conditions (e.g. Müller, 1978; Paul et al. 1990, Sanft and Wyss, 1990). Dominant resistance genes are being mapped in some of these varieties (e.g. potato, Barone et al., 1990; tomato, Williamson, 1990) but the complexity of the genomes of these crop plants as well as the complexity of the plant-nematode interaction under laboratory conditions has prevented isolation of such genes to the present day. Most of the progress in the techniques of plant-gene isolation with the help of Restriction Fragment Length Polymorphism (RFLP)-mapping and chromosome walking (Bleecker et al. 1991), T-DNA insertion mutagenesis (Feldmann, 1991) or transposon-mutagenesis (Altmann et al. 1991) is accomplished with a small crucifer *Arabidopsis thaliana*. The genome size, the short generation time and the well developed classical genetics for this species are at the basis of this progress. One important factor for the isolation of a gene of interest is the ability to screen phenotypically for the dominant presence of the gene in crossings with lines that are recessive for that trait. One major drawback of Arabidopsis in the identification of resistance genes is the limited number of plant-pathogens that are able to infect on this species. Known examples are now limited to a few bacteria (Simpson and Johnson, 1990; Whalen et al., 1991) and fungi (Koch and Slusarenko, 1990). Successful infection of Arabidopsis with plant-parasitic nematodes, both in soil or under monoxenic conditions, has never been reported in the literature, despite the fact that nematodes can be major pests in agronomically important cruciferous plants as sugarbeet and rapeseed. Standard conditions used in nematology and plant tissue culture does not lead to successful infection of nematodes on Arabidopsis in soil or in tissue culture (unpublished results, MOGEN, Leiden, NL; Dept. Phytopathology, Univ. Kiel, Germany; Rothamsted Expt. Station, Harpenden, UK).

SUMMARY OF THE INVENTION

Figure 1:
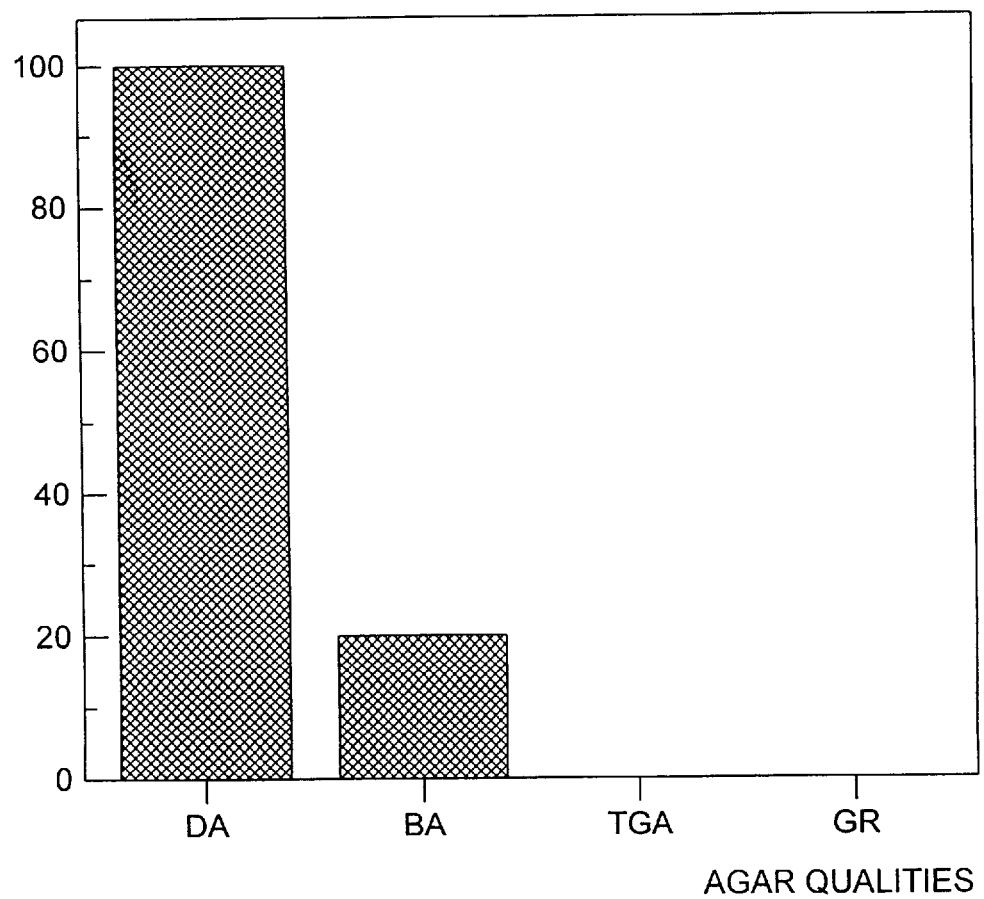
FIG. 1. Effects of Agar type on infection of *Heterodera schachtii* on *Arabidopsis thaliana*. The inoculation with nematodes was done 10 d after germination. The medium used to dissolve the different agars was optimal medium according to this invention. Results are expressed as a percentage of the mean number of infections in Daichin agar (n=45). DA=Daichin Agar, BA=Difco Bacto agar, TGA=technical grade agar, GR=Gelrite. All agar concentrations were 0.8% (w/v). Gelrite was at 0.25% because of its higher water-retaining capacity.

The invention provides a method for infecting a root of a plant of the genus Arabidopsis with a plant parasitic nematode under monoxenic conditions, comprising the steps of:

(a) contacting the root with a plant parasitic nematode in the presence of a highly purified gelling matrix dissolved in a nutrient medium that is devoid of nematode inhibiting substances, (b) allowing the nematode to infect the root by forming a feeding structure.

Another embodiment of the invention is a method for the screening of an ecotype or a mutant of Arabidopsis for its relative resistance to a plant parasitic nematode, comprising the steps of:

(a) infecting the ecotype with a plant parasitic nematode using a method as above, and (b) counting the number of nematode feeding structures formed in the roots of said ecotype.

A further preferred embodiment of the invention is a monoxenic plant root system of a plant of the genus Arabidopsis, comprising a root supporting substance in a suitable nutrient medium which is devoid of nematode inhibiting substances, and a root which is infected with a plant parasitic nematode, whereby said root has at least one nematode feeding structure. A more preferred embodiment comprises a monoxenic plant root system, wherein the root supporting substance is a highly purified gelling matrix. A still further preferred embodiment is a monoxenic plant root system according to the invention, wherein said highly purified gelling matrix comprises 0.8% Daichin agar solution in a nutrient medium, more preferably, wherein the medium contains 1% sucrose.

The invention finds specific use in a method for the isolation of a gene involved in resistance to a plant parasitic nematode from an ecotype of Arabidopsis, comprising the steps of:

(a) selecting an ecotype with a relatively high resistance to said plant parasitic nematode identified using any one of the methods above, and (b) crossing said relatively resistant ecotype with a different ecotype which is relatively susceptible to infection against said plant parasitic nematode and which has a defined genetic background in terms of screenable genetic markers, (c) linking the said gene involved in resistance to the plant parasitic nematode to one of said screenable markers through a series of back-crossings of the most resistant progeny of said crossings with said relatively susceptible ecotype, until a sufficiently close linkage of said gene with said screenable markers has been obtained to isolate the gene involved with resistance, (d) isolating the said gene involved in resistance to said plant parasitic nematode on the basis of said linkage.

Further embodiments of the invention comprise genes involved in relative resistance to a plant parasitic nematode obtained using a method of the preceding paragraph.

Yet another embodiment of the invention comprises a method for the isolation of a promoter that is capable of driving the expression of a gene in a nematode feeding structure from a plant of the genus Arabidopsis, comprising the steps of:

(a) transforming a plant cell of the genus Arabidopsis with a recombinant polynucleotide which contains a structural coding sequence encoding a screenable or selectable marker which is devoid of a promoter that is active in a plant, (b) generating a whole transformed plant from the cell transformed in step (a), (c) infecting the roots of said plant obtained in step (b) with a plant parasitic nematode capable of causing a feeding structure in said roots using a method according to any one of the methods above, (d) selecting plants the roots of which have feeding structures, (e) selecting a plant root wherein the selectable or screenable marker is present in said feeding structure, and (f) isolating the promoter that is upstream of the structural coding sequence encoding the selectable or screenable marker, causing the expression of said structural coding sequence, from the genome of the plant selected in step (e). The invention also comprises a promoter obtained using the said method.

DETAILED DESCRIPTION OF THE INVENTION

It was found that a range of nematode species (among which the cyst nematodes *Heterodera schachtii, H. trifolii, H. cajani,* the root-knot nematodes *Meloidogyne incognita* and *M. arenaria* and the migratory nematode *Pratylenchus penetrans*) can be grown on roots of *Arabidopsis thaliana* under monoxenic conditions if the medium at least comprises a root supporting substance, which preferably comprises a highly purified gelling matrix (such as a tissue-culture-quality agar) that meets the following requirements; a) the matrix has sufficient water-retaining capacity but provides enough mechanical support for invasion of infective nematode juveniles into roots of Arabidopsis, it is able to dissolve in used nutrient solutions at physiological pH, autoclavable prior to gelling and preferably transparent for routine analysis of infected root systems, b) a nutrient solution that is optimized for hydroponic root culture in combination with plant parasitic nematodes. c) and essentially void of any nematode-inhibiting substances. A preferred gelling matrix comprises a tissue-culture-quality agar (e.g. Daichin agar) dissolved in a suitable nutrient medium. A suitable medium can be selected from known tissue culture media such as Murashige & Skoog medium (1962), or media used for nematode cultures on plant roots (Dropkin & Boone, 1966). Especially good results can be obtained by using a medium containing: 2.5 mM $K^+$, 1.27 mM $Ca^{2+}$, 0.2 mM $Mg^{2+}$, 2.54 mM $NO_3^-$, 0.5 mM $H_2PO_4^-$, 0.2 mM $SO_4^{2-}$, 2 $\mu$M $Na^{2+}$, 1.8 $\mu$M $Mn^{2+}$, 0.14 $\mu$M $Zn^{2+}$, 60 nM $Cu^{2+}$, 24 nM $Co^{2+}$, 24 $\mu$M $Cl^-$, 9 $\mu$M $BO_3^{3-}$, 60 nM $MoO_4^{2-}$, 20 $\mu$M $Fe^{3+}$NaEDTA, pH 6.4, 1% (w/v) sucrose and 0.8% (w/v) Daichin agar, hereinafter referred to as the Sijmons medium. Further optimizations of culture media can be done to improve the infection rate of a particular nematode-Arabidopsis interaction, which are within the scope of this invention. All the mentioned nematode species showed multiple infections on single root systems in the said medium and were able to make complete life cycles while parasitizing Arabidopsis roots. Juveniles of *Globodera rostochiensis* were able to infect the roots under these monoxenic conditions but a strong necrosis at the site of infection prevented further development of the nematode. Juveniles of *Heterodera goettingiana* were strongly stimulated by Arabidopsis roots in agar but the roots were destroyed at the site of invasion and no developing juveniles could be observed.

A preliminary screen of 74 different ecotypes of Arabidopsis for resistance against *H. schachtii* resulted in a range of infection rates (between 1.7 and 11.1 females/plant). This indicates that the genetic background of the Arabidopsis ecotype does influence the pathogenicity of the nematode. Hence we predict the possibility to identify and isolate dominant resistance genes from this plant using the techniques from the present state of the art in molecular biology. The number of successful infections can be scored easily (without staining or destructive root analysis) under monoxenic conditions. This eliminates the use of soil during screening and further adds to the potential of the monoxenic culture system. Plants that score favourably when assayed for nematode resistance can immediately be brought to flowering conditions for seed harvest. Feeding-structures that develop inside the roots can be seen at low magnification and are easy to isolate with a minimum of contaminating cells. These feeding-structures are an excellent source for RNA's that are specifically expressed in these structures. This allows the isolation, preferably using molecular enrichment procedures (Dickinson et al., 1991) of genes corresponding to these RNA's. Using an (anti)sense approach, where the (anti)sense gene is directed against an essential gene for the development or maintenance of feeding structures can be specifically inhibited. Alternatively, the promoters that are associated with such essential genes can be used to drive the expression of genes inhibiting normal feeding-structure development or a normal feeding behaviour of the nematode.

The development of culture conditions for obligate nematodes on ecotypes of *Arabidopsis thaliana* offers formerly unknown possibilities to develop plants with increased resistance against plant parasitic nematodes.

The following aspects are outlined in some detail for purposes of illustration only and are not intended to limit the scope of this invention, as a skilled person may design alternative approaches.

I A first typical approach for obtaining nematode resistance genes, which can be introduced into economically important crop plants in order to increase their resistance against plant-parasitic nematodes, will generally involve the following steps, 1) Screening of Arabidopsis ecotypes for resistance against nematodes by infecting roots with a compatible (i.e. infectious) nematode using an infection method according to the invention, selecting a resistant plant line, and preferably making the ecotype isogenic through repeated backcrosses, 2) Mapping the gene or genes determining the resistance through crosses of the (isogenic) resistant line with *Arabidopsis thaliana* ecotype Columbia or Landsberg erecta, or other ecotypes which have well-defined genetic backgrounds and are susceptible to the nematode, again using the medium conditions according to the invention, for the screening of nematode resistance of the offspring, 3) Isolate the mapped nematode resistance (NR) gene from the said resistant ecotype, by using gene tagging methods such as T-DNA insertion mutagenesis (Feldmann, 1991), transposon-tagging (Altmann et al. 1991) or RFLP mapping followed by chromosome walking (Bleecker et al., 1991). In the first method, Agrobacterium is used to perform saturation mutagenesis through the insertion of T-DNA's after which the transformed population is screened for mutants in the resistance gene. Probing with T-DNA fragments and inverted PCR amplification allows the isolation of the flanking sequences. These in turn make it possible to clone surrounding DNA fragments that can be re-transformed into the mutant line, allowing a phenotypic selection of clones containing the NR-gene. For the second method, it has been shown that transposons, such as Ac transposase, also work in heterologous plant species such as tomato (Dickinson, 1991) or Arabidopsis (Altmann et al., 1991). A transgenic plant line is selected carrying an Ac element that is closely linked to the NR-gene (by RFLP mapping) which can then be used for transposon mutagenesis of the NR-gene. Probing with Ac sequences and inverted-PCR amplification allows the isolation of flanking sequences followed by the steps described above for the first method. The third method involves RFLP-mapping followed by chromosome walking in order to identify and isolate the NR-gene (Bleecker, 1991).

4) Identify and isolate a promoter, e.g. through promoter analysis with marker genes such as glucuronidase, that is functional in the plant to be protected at the site of infection;

5) Cloning the said NR-gene behind the promoter, in an expression cassette. In many cases also the entire resistance gene, with its own promoter, can be used directly after cloning in an expression cassette.

6) Introduce the expression cassette into plant material from which new plants can be generated.

7) Generate whole new plants from the transformed plant material.

Subsequently, transformed plants on which nematodes can be cultured can be assayed for nematode resistance through growth of the plants in soil infected with nematodes or under monoxenic conditions using an infection method according to this invention.

II A second typical approach for obtaining nematode resistance gene, which can be introduced into economically important crop plants in order to increase their resistance against plant-parasitic nematodes, will generally involve the following steps, 1) screening of Arabidopsis ecotypes or mutants of a resistant ecotype for susceptibility against nematodes by infecting roots with an incompatible (i.e. non-infectious) nematode (e.g. *Globodera rostochiensis* or *H. goettingiana*) using an infection method according to the invention, selecting a susceptible plant line, and preferably making the ecotype isogenic through repeated backcrosses, 2) mapping the resistance gene from e.g. *Arabidopsis thaliana* ecotype Columbia or Landsberg erecta through crosses with the (isogenic) susceptible ecotype or mutant, again using the medium conditions according to the invention, 3) to 7) as described for the first approach.

It should be understood that for the purposes of this description the term "resistance gene" is not limited to genes involved in recognition reactions as described by the gene-for-gene model. In mutant screens with a compatible nematode, as described by the first approach, mutated genes may be encountered that are essential for steps after the initial recognition phase such as feeding-structure induction or maintenance. As mutations in such essential genes, hereinafter referred to as 'Essential Genes' will give phenotypical resistance in the culture conditions as described in this invention, the genes carrying such a mutation can be identified.

III the following steps will illustrate a third typical approach for obtaining nematode resistance genes of the latter category, which can be introduced into economically important crop plants in order to increase their resistance against plant-parasitic nematodes, 1) Identify mutations in Essential Genes that are essential for any step in the pathogenicity of parasitic nematodes by screening for resistance in mutants of a susceptible ecotype of Arabidopsis by infecting roots with a compatible nematode, using a method according to the invention.

2) mapping the resistance gene through crosses with e.g. *Arabidopsis thaliana* ecotype Columbia or Landsberg erecta, 3) isolating the wild type equivalent of the mutant gene (if mutation is recessive) or the mutant gene directly (if the mutation is dominant) from the said mutant, including its promoter, by complementation experiments as e.g. described in step 3 of approach I.

4) cloning the said wild-type gene in an antisense direction behind asuitable promoter, and then steps 5)–7) as described for the first approach with the proviso that the NR-gene is in the antisense direction with respect to the promoter.

Alternatively, one can also make use of the 'sense' approach (Napoli et al. 1990; Van der Krol et al. 1990) in which in special cases the activity of the endogenous gene is suppressed by expression of the incoming homologous gene.

In this approach (III), the NR-gene is in fact an (intact) 'Essential-Gene' which is overexpressed, but as a result of the inhibitory effect resulting from the overexpression, the 'Essential Gene' becomes a nematode resistance gene according to the invention.

IV Alternatively, resistance genes as isolated from Arabidopsis in the third approach described above, can be used as probes to isolate homologous genes and their particular promoter from other plant species that are of agronomic importance.

V Alternatively, the culturing method provides a way for easy enrichment of feeding-structure tissue, without the need of synchronized infection or dissecting said structure from the roots. The feeding-structures that develop inside the roots of Arabidopsis obtain several times the size of the surrounding epidermal and parenchymal tissue and are therefore easy to isolate with a minimum of contaminating cells, even at low magnification. Messenger-RNA isolated from such an enriched tissue sample can be used for the development and screening of substraction cDNA libraries (Dickinson et al., 1991), for the identification of genes that are specifically expressed at this stage of infection. Through this procedure, genes that are specific for feeding-structure tissue and possibly essential for the induction or maintenance of the feeding-structure can be isolated and used in an (anti)sense approach that is similar to that described above in approach III.

VI The root system according to the invention can be conveniently used for the isolation of promoters that are capable of expressing genes in the feedig structures, prefereably resistance genes. Such promoters are isolated, for instance via interposon tagging (Topping et al., 1991, Developm. 112, 1009–1019; Koncz, C. et al., (1989) Proc. Nat. Acad. of Sci. U.S.A. 86, 8467–8471). The random integration of the T-DNA enables the identification of promoter sequences that are active in the feeding structures. This type of interposon tagging of promoter sequences is especially well established in Arabidopsis (Kertbundit et al., 1991, Proc. Nat. Acad. Sci. USA 88, 5212–5216) and tobacco (Topping et al., 1991, Developm. 112, 1009–1019). The tagged promoter sequences upstream of the GUS structural coding sequence can for instance be isolated with inverted polymerase chain reaction (Does et al. 1991, Plant Mol. Biol. 17, 151–153). Once suitable regulatory sequences are identified or genes that are transcribed inside the feeding structure, they can be used as probes for the isolation of homologous sequences from other plant species.

The following examples further illustrate the invention.

EXPERIMENTAL

The methods described in this section for maintenance and sterilization of nematode species are routine procedures in the art of Nematology and do not part of the invention.

Cultivation of Plants

Arabidopsis seeds were soaked 2 min in 70% EtOH and surface sterilized either for 5 min in 0.8% $Ca(OCl_2)$, 0.05% Tween 20 or for 8 min in 5% $Ca(OCl_2)$, 0.05% Tween 20, depending on the degree of contamination of the seeds. Sterilized seeds were washed at least 3 times in sterile water and transferred to agar containing growth media.

The optimal medium for monoxenic development of nematodes contained: 2.5 mM $K^+$, 1.27 mM $Ca^{2+}$, 0.2 mM $Mg^{2+}$, 2.54 mM $NO_3^-$, 0.5 mM $H_2PO_4^-$, 0.2 mM $SO_4^{2-}$, 2 $\mu$M $Na^{2+}$, 1.8 $\mu$M $Mn^{2+}$, 0.14 $\mu$M $Zn^{2+}$, 60 nM $Cu^{2+}$, 24 nM $Co^{2+}$, 24 $\mu$M $Cl^-$, 9 $\mu$M $BO_3^{3+}$, 60 nM $MoO_4^{2-}$. Fe was added as 20 $\mu$M $Fe^{3+}$NaEDTA. The pH was adjusted to 6.4 with 1 N KOH. Just prior to sterilization (20 min 110° C.), 1% (w/v) sucrose and 0.8% (w/v) Daichin agar (Brunschwig Chemie BV, POB 70213, Amsterdam, The Netherlands) was added. Both 9 cm Petri dishes with 15 seeds or 24-well tissue culture plates (Greiner, Germany) with 2 seeds per well were used to study media conditions. Ecotype screening was done in the 24-well plates. For testing of different nematode species, seeds were arranged in a row on the top half of a Petri dish. After a 3 d germination period, the plates were slightly tilted to let the roots grow downwards. The plates were sealed with Parafilm and kept at 23°–25° C. with 16 hr L/8 hr D.

Maintenance of Nematode Populations.

The different nematode species used in these studies were either maintained in pot cultures or sampled from field populations on their respective hosts as indicated in Table 1. Monoxenic stock cultures of *H. schachtii* were maintained in vitro on *Sinapis alba* cv. Albatros for 6 weeks and stored at 4° C. until use (Grundler, 1989).

Sterilization of Nematode Species

Egg-suspensions were prepared from crushed fresh cysts or hand-picked egg masses in the case of Meloidogyne. The suspension was placed on a sterile Swinnex disc filter holder with a cellulose nitrate membrane (Schleicher & Schuell, pore size 5 $\mu$m) or on 20 $\mu$m nylon gauze fixed in a plastic ring. The eggs on the filter were exposed to 0.1% $HgCl_2$ for 4 min and washed 4 times with 5 ml sterile water (Grundler, 1989). The sterile eggs were scooped off the membrane onto the agar surface.

Deposit of microorganisms

Binary vector pMOG23 has been deposited in *E. coli* K-12 strain DH5α, deposited at the Centraal Bureau voor Schimmel-cultures on Jan. 29, 1990 under accession number CBS 102.90).

EXAMPLE 1

Culture conditions for infection of Arabidopsis

Aseptic cysts of *H. schachtii* containing $J_2$ were either cut open directly in the vicinity of growing root tips, or transferred on a 200 $\mu$m mesh plastic sieve and placed in a sealed glass funnel containing a 3 mM $ZnCl_2$ hatching stimulant solution. After 3 d dark incubation (25° C.), hatched $J_2$ could be harvested, washed 3 times with sterile water and suspended in 0.5% Gelrite for reproducible inoculations. Inoculations were done 7–10 days after sowing, either with crushed cysts or with 25–70 juveniles per plant, depending on the type of experiment. All procedures were performed under aseptic conditions on a minimum of 45 plants.

Figure 2:
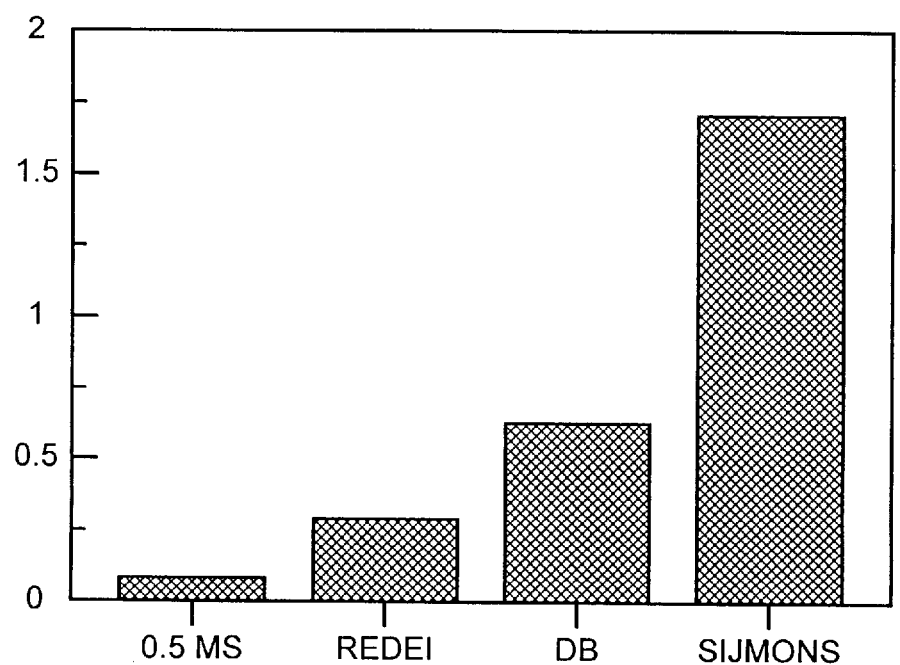
FIG. 2. Medium effects on infection of *Arabidopsis thaliana* type Landsberg erecta with *Heterodera schachtii*. Mean number of females/plant grown in different media (n=45); 0.5 MS=half strength Murashige and Skoog (1962) medium, DB=Dropkin and Boone (1966) medium, Redei (1965) medium, Sijmons=medium according to this invention.
Figure 3:
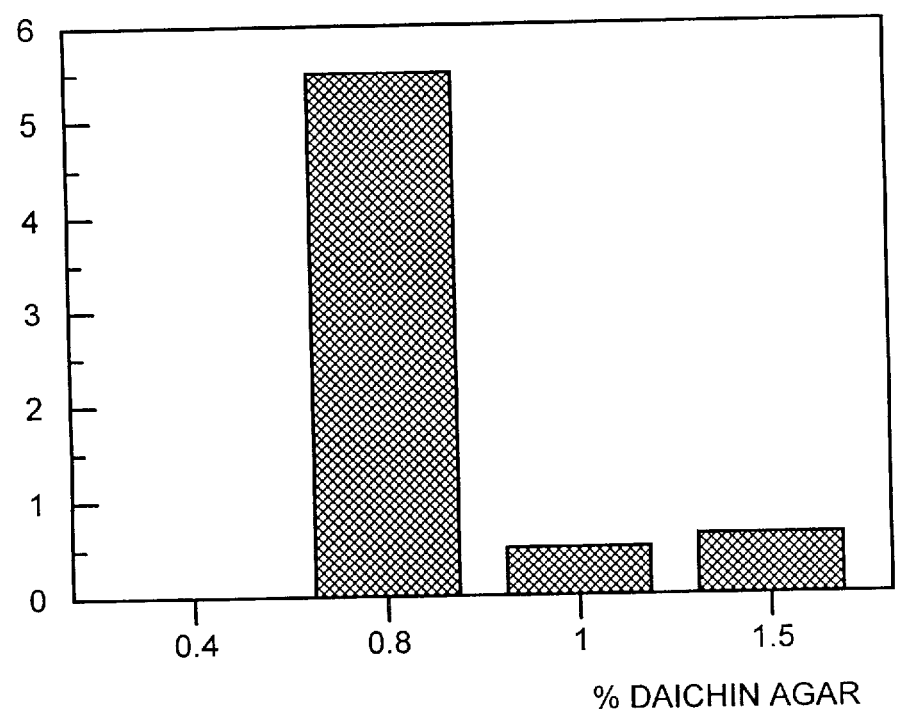
FIG. 3. Effect of Daichin agar concentration on infection of *Arabidopsis thaliana* type Landsberg erecta with *Heterodera schachtii*. The medium was Sijmons medium according to this invention. Mean number of successful infections per plant (n=45).
Figure 4:
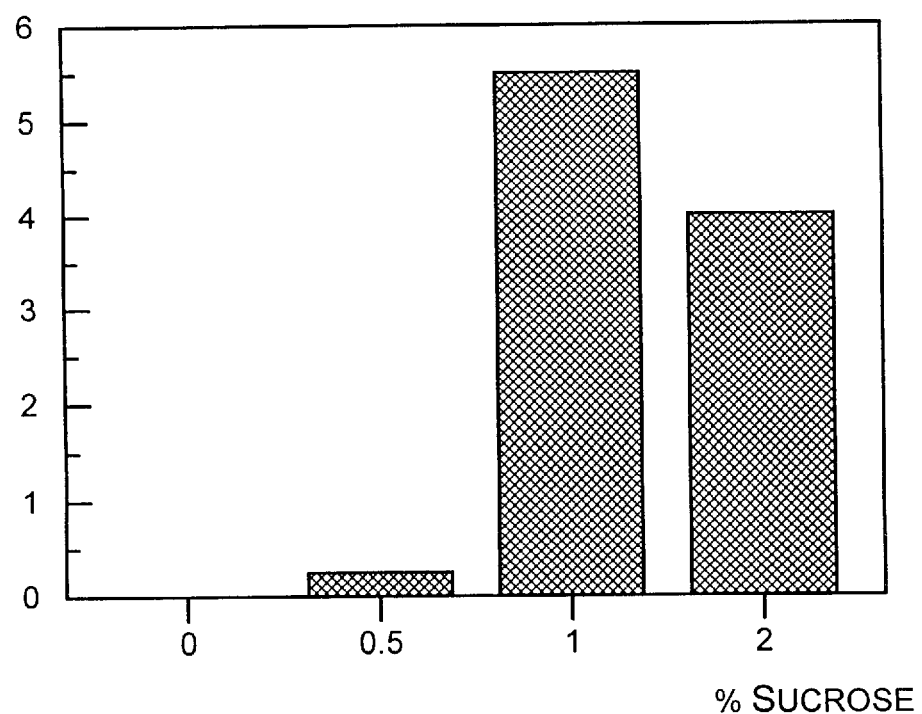
FIG. 4. Effect of sucrose concentration on infection of *Arabidopsis thaliana* type Landsberg erecta with *Heterodera schachtii*. The medium was Sijmons medium according to this invention. Mean number of successful infections per plant (n=45).

The effects of different agar qualities on the number of successful infections in monoxenic culture are illustrated in FIG. 1. The effects of different media, sucrose concentration and Daichin agar concentration on the number of developing females per plant or the number of successful infections per plant are illustrated in FIG. 2. The following Arabidopsis ecotypes were tested: An-1, Ba-1, Bch-1, Bl-1, Bla-1, Bn-0, Bor-0, Cal-0, Chi-0, Ci-0, Co-4, Col-0, Ct-1, Cvi-0, Edi-0, En-2, Esc-0, Est-0, For-1, Gd-1, Gö-0, Gre-0, Ha-0, Hl-0, Hm-0, Hs-0, Ita-0, Kä-0, Kil-0, Kin-0, Kl-0, Kr-0, La-0, La-er, Lan-0, Lc-0, Ll-0, Map-0, Mc-0, Mh-0, Mr-0, Ms-0, Old-2, Ove-0, Pa-3, Per-1, Pi-0, Pla-0, Po-0, 0, Pt-0, Rou-0, Rsch-0, Sac-0, Sah-0, Se-0, Sei-0, Set-0, Sf-0, Sr-0, Stw-0, Su-0, Sue-0, Sy-0, Ts-1, Tu-0, Tul-0, Ty-0, Wa-1, Wc-1, Wil-3, Ws-0, Wt-1, Yo-0, Ze-0. The codes are according to the population codes of the AIS-Seed bank listings (Kranz and Kirchheim, 1987). The most resistant ecotypes (i.e. the lowest mean number of developing females per plant) were Sah-0, Lan-0, and Kil-0. The most susceptible ecotypes were Gre-0 and La-0. Presently Sah-0 and Lan-0 are the best candidates for mapping resistance genes. We predict that upon further screening of ecotypes more, putatively even absolutely, resistant ecotypes will be found, which will be most preferred for use in mapping NR-genes.

Nematode species tested on Arabidopsis

The different nematode species that were tested for infectivity and completion of lite cycles are mentioned in Table 1. Except for *G. rostochiensis* and *H. goettingiana,* all other nematode species mentioned in Table 1 did have complete life cycles on Arabidopsis roots using medium according to the invention. The medium was optimized for *H. schachtii* and need not be the most optimal for the other species tested. Specific ion- and sucrose-concentrations, buffer types and gelling matrices may be optimized further according to specific requirements of a plant-parasitic nematode species. The nematode species mentioned in Table 1 are offered by way of illustration and not by way of limitation.

EXAMPLE 2

Construction of a promoterless GUS gene construct

Figure 5:
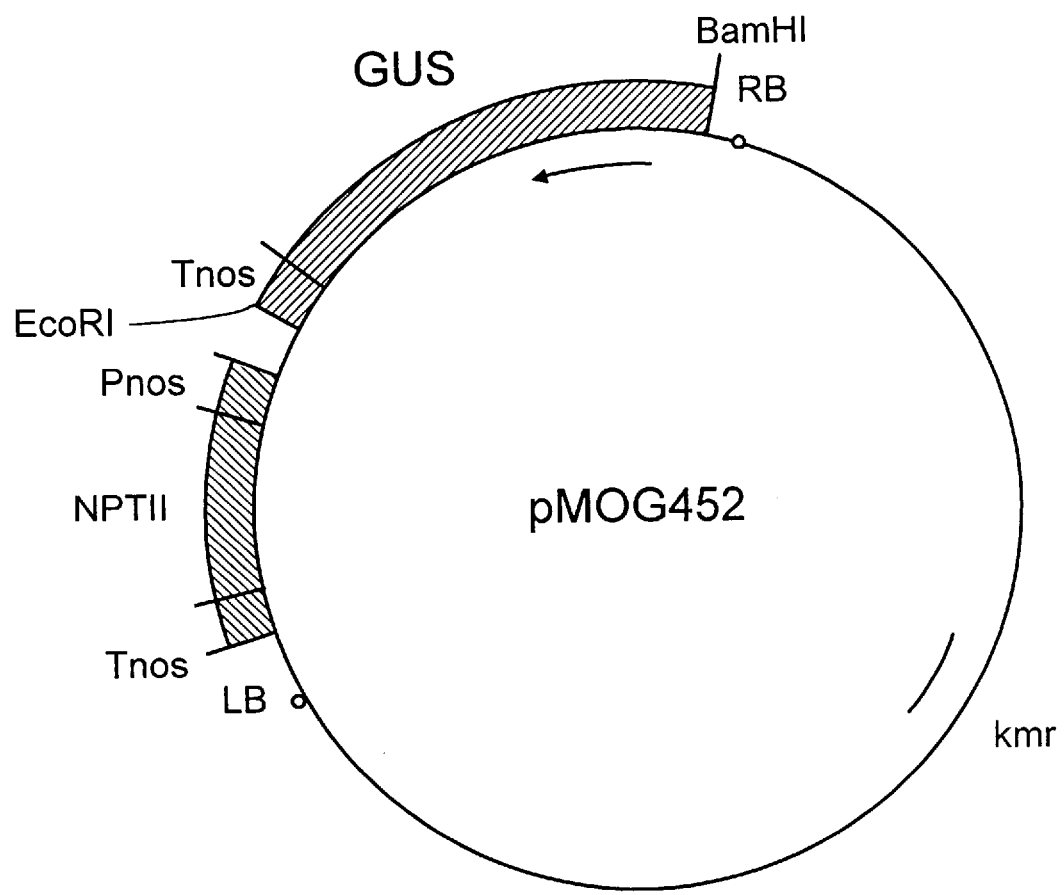
FIG. 5. Binary vector pMOG452. This plasmid is a derivative of pMOG23 and contains a promoterless GUS construct to 'fish' for promoters that can be used for expression of genes in a nematode feeding structure.

The gene coding for GUS fused to a 3'nos terminator sequence but without any 5' regulatory promoter sequences was cloned as a EcoRI-BamHI fragment from pBI101 plasmid (Jefferson, 1987, Plant Mol. Biol. Reporter 5, 387–405) into the multiple cloning site of binary vector pMOG23, resulting in binary plasmid pMOG452 (FIG. 5). pMOG452 was introduced into *Agrobacterium tumefaciens* strain MOG101 by triparental mating from *E.coli,* using HB101 pRK2013) as a helper. Transconjugants were selected for resistance to rifampicin (20 mg/l) and kanamycin (100 mg/l).

EXAMPLE 3

Construction of Agrobacterium strain MOG101

A binary vector system was used to transfer gene constructs into Arabidopsis plants. The helper plasmid conferring the *Agrobacterium tumefaciens* virulence functions was derived from the octopine Ti-plasmid pTiB6. MOG101 is a *Agrobacterium tumefaciens* strain carrying a non-oncogenic Ti-plasmid (Koekman et al. 1982, Plasmid 7, 119–132) from which the entire T-region was deleted and substituted by a bacterial Spectinomycin resistance marker from transposon Tn 1831 (Hooykaas et al., 1980 Plasmid 4, 64–75).

Figure 6:
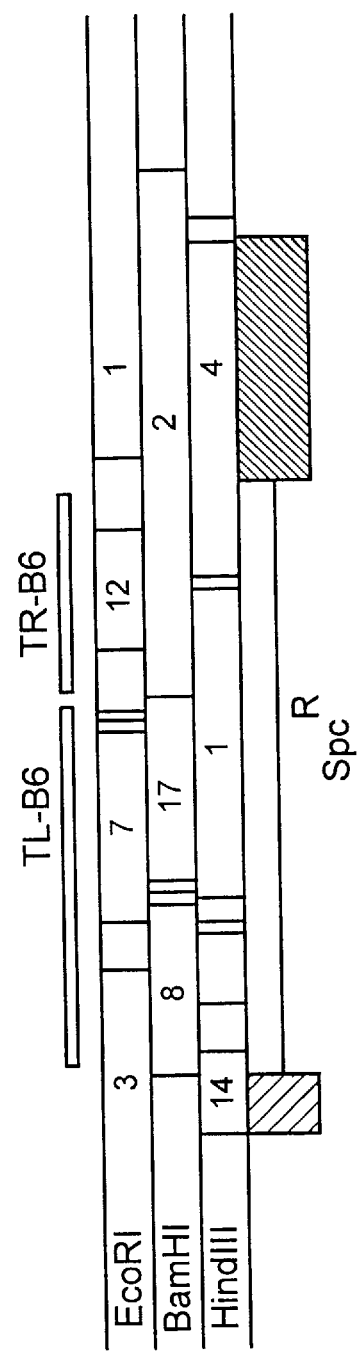
FIG. 6. Restriction map of fragment of Ti-plasmid pTiB6 used for the construction of a disarmed helper plasmid.
Figure 7:
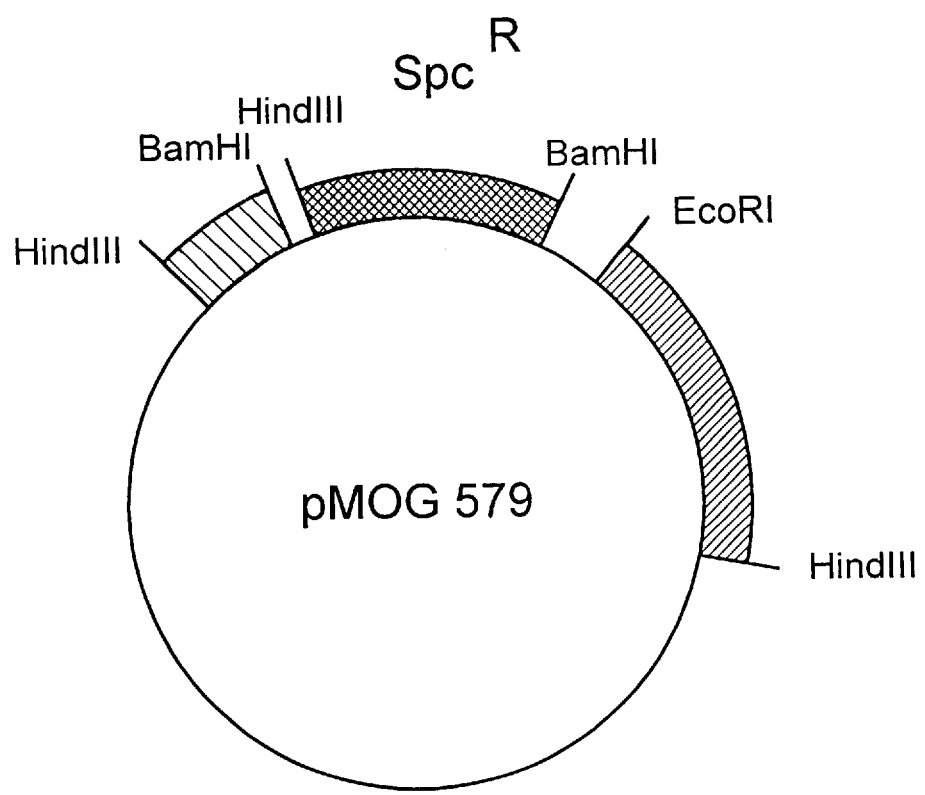
FIG. 7. Intermediate vector pMOG579, used to create the disarmed helper of Agrobacterium strain MOG101 which was used for Arabidopsis transformation.

The Ti-plasmid pTiB6 contains two adjacent T-regions, TL (T-left) and TR (T-right). To obtain a derivative lacking the TL- and TR-regions, we constructed intermediate vector pMOG579. Plasmid pMOG579 is a pBR322 derivative, which contains the 2 Ti-plasmid fragments that are located to the left and right, outside the T-regions.(FIG. 6). The 2 fragments (shown in dark) are separated in pMOG579 by a 2.5 kb BamHI-HindIII fragment from transposon Tn1831 (Hooykaas et al., 1980 Plasmid 4, 64–75) carrying the spectinomycin resistance marker (FIG. 7). The plasmid was introduced into *Agrobacterium tumefaciens* strain LBA1010 [C58-C9 (pTiB6) which is a cured C58 strain in which pTiB6 was introduced (Koekman et al. (1982), supra), by triparental mating from *E.coli,* using HB101 pRK2013) as a helper. Transconjugants were selected for resistance to Rifampicin (20 mg/l) and spectinomycin (250 mg/l). A double recombination between pMOG579 and pTiB6 resulted in loss of carbenicillin resistance (the pBR322 marker) and deletion of the entire T-region. Of 5000 spectinomycin resistant transconjugants replica plated onto carbenicillin (100 mg/l) 2 were found sensitive. Southern analysis showed that a double crossing over event had deleted the entire T-region (not shown). The resulting strain was called MOG101.

EXAMPLE 4

Transformation of Arabidopsis with pMOG452

Arabidopsis is transformed with Agrobacterium strain MOG101 containing the binary vector pMOG452. Transformation is carried out using co-cultivation of *Arabidopsis thaliana* (ecotype C24) root segments as described by Valvekens et al. (1988, Proc. Nat. Acad. Sci. USA 85, 5536–5540). Transgenic plants are regenerated from shoots that grow on selection medium (50 mg/l kanamycin), rooted and transferred to germination medium or soil.

Transgenic plant lines (T2 or later generations) are used for infection with plant parasitic nematodes and subsequently used for GUS analysis in the feeding structures. The GUS assay in the feeding structures can be carried out substantially the same way as described for plant leaves (Jefferson, 1987, Plant Mol. Biol. Reporter 5, 387–405). The dissected roots containing a feeding structure are assayed while still inside the agar; alternatively the agar can be removed before staining.

The results from such a screening experiment after inoculation with *H. schachtii* showed a surprisingly high number of plants with GUS activity inside the feeding structure and low or no GUS activity in other plant parts, thus indicating that regulatory sequences that drive gene expression inside the feeding structure are tagged by the promoterless GUS gene construct. One in 13 independent transgenic plant lines indicated a tagged promoter that was active in the feeding structure cells. This high frequency illustrates the feasibility to tag, and subsequently isolate a promoter that can suitably be used for the expression of nematode resistance gene in a plant cell.

EXAMPLE 5

Isolation of promoter from transgenic plants expressing GUS inside the feeding structure Transgenic plant lines that express GUS activity inside the feeding structure are selected and used for isolation of genomic DNA. Regulatory sequences upstream (5') of the integrated GUS gene is isolated using inverted PCR (Does et al. 1991, Plant Mol. Biol. 17, 151–153) with the primers 5'-CCAGACTGAATGCCCACAGGC-3' (SEQUENCE ID NO:1) and 5'-GGTGACGCATGTCGCGCAAG-3' (SEQUENCE ID NO:2). The amplified fragment is used to screen a genomic library of Arabidopsis for the isolation of a genomic clone that contains a suitable promoter for expression of a gene inside the feeding structure.

Alternatively, the first 200 bp of the GUS gene are used to probe a genomic bank made from the selected plants.

REFERENCES

Altmann, T., Jessop, A., Morris, P. C., Schmidt, R., Willmitzer, L. (1991) J. Cell. Biochem. Suppl 15A, p. 110.

Barone, A., Ritter, E., Schachtschabel, U., Debener, T., Salamini, F. and Gebhardt, C. (1990) Mol. Gen. Genet. 224, 177–182.

Bleecker, A. B. (1991) J. Cell. Biochem, suppl 15A, p.23

Dellaert L. M. W., Meijer, K. (1986) Zaadbelangen 7, 167–170.

Dickinson, M., Jones, D., Harrison, T. K., English, J., Bishop, G., Scofield, S., Hammond-Kosack, K., Jones, J. D. G. (1991) Adv. Mol. Gen. Plant-Microbe Interactions, 1, 276–279.

Dropkin, V. H. (1988). Ann. Rev. Phytopath. 26, 145–161.

Dropkin, V. H. and Boone, W. R. (1966). Nematologica 12, 225–236.

Feldmann, K. A. (1991) J. Cell. Biochem suppl 15A, p.26.

Gabriel, D. W. and Rolfe, B. G. (1990). Ann. Rev. Phytopathol. 28, 365–391.

Grundler, F. (1989). Thesis, University of Kiel, Germany.

Jones, F. G. W. Parrott, D. M. Perry, J. N. (1981) In: Plant Parasitic nematodes, Vol.3 (ed. B. M. Zuckerman & R. A. Rohde), pp 23–36. Acad. Press, New York Koch, E. and Slusarenko, A. (1990) Plant Cell 2, 437–445.

Kranz, A. R. and Kirchheim, B. (1987). Arabidopsis Inf. Serv. 24, 1–368.

Müller, J. (1978). Revue Nématol. 1, 47–52

Murashige M. and Skoog F. (1962) Physiol. Plant. 15: 473–497

Napoli, C., Lemieux, C., Jorgensen, R. (1990) Plant Cell 2, 279–289.

Omwega, C. O., Thomason, I. J., Roberts, P. A. (1990) Phytopath 80, 745–748.

Paul, H., Van Deelen, J. E. M., Henken, B., De Bock, T. S. M., Lange, W. and Krens, F. A. (1990) Euphytica 48, 153–157.

Rédei, G. P. (1965) Amer. J. Bot. 52, 834–841.

Rick, C. M. Fobes, J. F. (1974) Tomato Genet Coop Rep 24, 25.

Sanft, U. and Wyss, U. (1990) Potato Res. 33, 55–66.

Sasser, J. N. and Freckman, D. W. (1987) World prospective on nematology: the role of the society. In: Vistas on Nematology, Eds. J. A. Veech, and D. W. Dickson. Hyatts Will, Maryland. pp. 7–14.

Simpson, R. B. and Johnson, L. J. (1990) Mol. Plant-Microbe Interact. 3, 233–237.

Turner S. J., Stone, A. R., Perry J. N. (1983) Euphytica 32, 911–917.

Van der Krol, A. R., Mur, L. A. Beld, M., Mol, J. N. M., Stuitje, A. R. (1990) Plant Cell 2, 291–299.

Whalen, M. C., Innes, R. W., Bent, A. F. and Staskawicz, B. J. (1991) Plant Cell 3, 49–59.

Williamson, V. M., Colwell, G., Mei, H. Ho, J. Y. (1990) Proc. 2nd Int. Nematol. Congress, Veldhoven, The Netherlands

TABLE 1

Nematode species on *Arabidopsis thaliana* type Landsberg erecta in monoxenic conditions.

| Nematode | Origin[1] | Last Host | Comments |
| --- | --- | --- | --- |
| *Heterodera schachtii* | RES/Kiel populations | oilseed rape, mustard | complete life cycle in ca. 6 weeks, necrosis at invasion and feeding site. |
| *H. trifolii* | RES field population | clover | complete life cycle in ca. 2 months. |
| *H. goettingiana* | RES field population | field beans | $J_2$ strongly stimulated by roots, destroy roots at invasion site, no developing juveniles observed. |
| *H. cajani* | India, 1 yr at RES | cowpea | complete life cycle in ca. 2 months. |
| *Globodera rostochiensis* | RES greenhouse | potato/Désirée | few attempts to invade, strong necrosis, no further development. |
| *Melidogyne incognita* | RES/Kiel populations | tomato/Pixie | complete life cycle in 4–5 weeks, little or no necrosis during invasion, galling, females not within gall. |
| *M. arenaria* | NCSU, since 1983 RES greenhouse | tomato/Pixie | complete life cycle in ca. 6 weeks, little or no necrosis during invasion, round galls. |
| *Pratylenchus penetrans* | Kiel/RES | carrots, maize | life cycle in 4 weeks, good development; eggs deposited inside and outside of roots, necrosis. |

[1]RES = Rothamsted Expt. Station, NCSU = North Carolina State University

We claim:

1. A plant root system comprising a root of a plant of the genus Arabidopsis, a root-supporting substance, a nutrient medium and a plant-parasitic nematode that causes at least one nematode feeding structure in said root for supporting development of the nematode for a complete life cycle, the root supporting substance and nutrient medium being suitable for supporting development of the nematode on the root for said complete life cycle, said root comprising the at least one nematode feeding structure supporting the development of said plant-parasitic nematode, said root supporting substance comprising a highly purified gelling matrix that provides sufficient water-retaining capacity and mechanical support for supporting said development, said root supporting substance being substantially devoid of nematode-inhibiting substances.

2. A plant root system according to claim 1, wherein said plant is of the species *Arabidopsis thaliana*.

3. A plant root system according to claim 1, wherein said plant parasitic nematode is selected from *Heterodera schachtii, Heterodera trifolii, Heterodera cajani, Meloidogyne incognita, Meloidogyne arenaria,* and *Pratylenchus penetrans*.

4. A plant root system according to claim 1, wherein the root supporting substance comprises a tissue-culture grade gelling-matrix dissolved in said nutrient medium.

5. A monoxenic plant root system according to claim 4, wherein the root supporting substance comprises 0.8% Daichin agar (w/v) in 2.5 mM $K^+$, 1.27 mM $Ca^{2+}$, 0.2 mM $Mg^{2+}$, 2.54 mM $NO_3^-$, 0.5 mM $H_2PO_4^-$, 0.2 mM $SO_{4hu\ 2-}$, 2 μM $Na^{2+}$, 1.8 μM $Mn^{2+}$, 0.14 μM $Zn^{2+}$, 60 nM $Cu^{2+}$, 24 nM $Co^{2+}$, 24 μM $Cl^-$, 9 μM $BO_3^{3-}$, 60 nM $MoO_4^{2-}$, 20 μM $Fe^{3+}$NaEDTA, 1% (w/v) sucrose, pH 6.4.

6. A plant root system according to claim 1, wherein the root supporting substance comprises 0.8% Daichin agar.

7. A plant root system as claimed in claim 1, wherein said nematode feeding structure comprises a DNA sequence with an open reading frame encoding a selectable or screenable marker.

8. A plant root system according to claim 7, wherein the open reading frame encoding the selectable or screenable marker is transcribed under the control of a promoter that is naturally present in the genome of the plant and is expressed in said feeding structure.

9. A plant root system according to claim 7, wherein the open reading frame encodes beta-glucuronidase.

10. A plant root system according to claim 7, wherein said plant is of the species *Arabidopsis thaliana*.

11. A plant root system according to claim 7, wherein said plant-parasitic nematode is a cyst nematode.

12. A plant root system according to claim 11, wherein said cyst nematode is *Heterodera schachtii*.

13. A plant root system according to claim 7, wherein the root supporting substance comprises a tissue-culture grade gelling-matrix dissolved in said nutrient medium.

14. A plant root system according to claim 7, wherein the root supporting substance comprises 0.8% Daichin agar.

15. A method comprising infecting a root of a plant of the genus Arabidopsis with a plant parasitic nematode for the production of at least one nematode feeding structure on the root for supporting development of the nematode for a complete life cycle by contacting the root with the plant parasitic nematode in the presence of a composition consisting essentially of a root supporting substance and a nutrient medium suitable for supporting the development of the nematode on the root for said complete life cycle, said root supporting substance comprising a highly purified gelling matrix that provides sufficient water-retaining capacity and mechanical support for supporting said development, said root supporting substance being substantially devoid of nematode-inhibiting substances.

16. A method as claimed in claim 15, wherein the root is from an ecotype or mutant of Arabidopsis and the method further comprises screening the root for the presence of feeding structures to calculate the number thereof, and determining a resistance of the ecotype or mutant from the number of feeding structures.

17. A root of a plant of the genus Arabidopsis made by the method of claim 15 wherein the at least one nematode feeding structure comprises a DNA sequence with an open reading frame encoding a selectable or screenable marker.

18. A root according to claim 17, wherein said nematode feeding structure is produced by a process comprising infecting the plant with a cyst nematode.

19. A root according to claim 18, wherein said cyst nematode is *Heterodera schachtii*.

20. A root according to claim 17, wherein the open reading frame encoding the selectable or screenable marker is transcribed under the control of a promoter that is naturally present in the genome of the plant and is expressed in said feeding structure whereby said selectable or screenable marker is detectably present in said feeding structure.

21. A root according to claim 17, wherein the open reading frame encodes beta-glucuronidase.

22. A root according to claim 17, which is of the species *Arabidopsis thaliana*.

23. A plant root system according to claim 3 wherein the root supporting substance is an agar selected from the group consisting of Daichin Agar and Difco Bacto Agar.

24. A method as claimed in claim 15 wherein the root-supporting substance and nutrient medium are suitable for supporting infection of the plant by more than one female nematode.

25. A method as claimed in claim 15 wherein the root-supporting substance and nutrient medium are suitable for supporting multiple infections of the plant by nematodes.

* * * * *

SEQUENCE LISTING ( 1 ) GENERAL INFORMATION:

( i i i ) NUMBER OF SEQUENCES: 2

( 2 ) INFORMATION FOR SEQ ID NO:1:

( i ) SEQUENCE CHARACTERISTICS:

(A) LENGTH: 21
(B) TYPE: Nucleic acid
(C) STRANDEDNESS: Single
(D) TOPOLOGY: Linear (i i) MOLECULE TYPE: cDNA (i i i) HYPOTHETICAL: Yes (x i) SEQUENCE DESCRIPTION: SEQ ID NO:1:

CCAGACTGAA TGCCCACAGG C 21

(2) INFORMATION FOR SEQ ID NO:2:

(i) SEQUENCE CHARACTERISTICS:
(A) LENGTH: 20
(B) TYPE: Nucleic acid
(C) STRANDEDNESS: Single
(D) TOPOLOGY: Linear (i i) MOLECULE TYPE: cDNA (i i i) HYPOTHETICAL: Yes (x i) SEQUENCE DESCRIPTION: SEQ ID NO:2:

GGTGACGCAT GTCGCGCAAG 20